US012721576B2

(12) United States Patent
Gulsun et al.

(10) Patent No.: US 12,721,576 B2
(45) Date of Patent: Sep. 1, 2026

(54) AI-BASED MEDICAL IMAGING ANALYSIS OF PHOTON COUNTING DATA

(71) Applicant: Siemens Healthineers AG, Forchheim (DE)

(72) Inventors: Mehmet Akif Gulsun, Princeton, NJ (US); Puneet Sharma, Princeton Junction, NJ (US); Max Schöbinger, Hirschaid (DE)

(73) Assignee: Siemens Healthineers AG, Forchheim (DE)

( * ) Notice: Subject to any disclaimer, the term of this patent is extended or adjusted under 35 U.S.C. 154(b) by 275 days.

(21) Appl. No.: 18/346,291

(22) Filed: Jul. 3, 2023

(65) Prior Publication Data

US 2025/0009314 A1 Jan. 9, 2025

(51) Int. Cl.
*A61B 6/03* (2006.01)
*A61B 6/42* (2024.01)
(Continued)

(52) U.S. Cl.
CPC ............ *A61B 6/035* (2013.01); *A61B 6/4241* (2013.01); *G06T 7/0012* (2013.01); *A61B 6/503* (2013.01); *G06T 2200/28* (2013.01)

(58) Field of Classification Search
CPC ..... A61B 6/032; A61B 6/4241; A61B 6/5217; A61B 6/5205; A61B 6/035; A61B 6/503; G06T 2207/10081; G06T 2207/20084; G06T 2207/20081; G06T 7/0012; G06T 2207/30004; G06T 2211/424; G06T 5/60; G06T 2200/28; G06V 10/82; G06V 2201/03; G16H 50/20; G16H 30/40; G06N 3/045; G06N 3/0464
See application file for complete search history.

(56) References Cited

U.S. PATENT DOCUMENTS 10,853,449 B1 * 12/2020 Nguyen ................. G16H 15/00
11,556,784 B2 * 1/2023 Luo .......................... G06N 3/04
(Continued)

FOREIGN PATENT DOCUMENTS

CN 110879949 B * 4/2023 ........... G06F 18/214
EP 3695784 A1 * 8/2020 ........... A61B 6/5217
WO WO-2014192935 A1 * 12/2014 ............ A61B 6/482

OTHER PUBLICATIONS

Arritt, Robert P., and Roy M. Turner. "Context-sensitive weights for a neural network." International and Interdisciplinary Conference on Modeling and Using Context. Berlin, Heidelberg: Springer Berlin Heidelberg, 2003. (Year: 2003).*
(Continued)

*Primary Examiner* — Courtney Joan Nelson

(57) ABSTRACT

Systems and methods for performing a medical imaging analysis task from PCCT (photon counting computed tomography) imaging data are provided. PCCT imaging data acquired from a PCCT imaging device is received. A plurality of PCCT virtual images is generated from the PCCT imaging data. A plurality of medical imaging analysis sub-tasks is performed based on the plurality of PCCT virtual images using a plurality of machine learning based networks. Results of the medical imaging analysis sub-tasks are combined to generate results of a medical imaging analysis task. The results of the medical imaging analysis task are output.

14 Claims, 6 Drawing Sheets

(51) Int. Cl.
*A61B 6/50* (2024.01)
*G06T 7/00* (2017.01)

(56) References Cited

U.S. PATENT DOCUMENTS

| | | | |
|---|---|---|---|
| 2018/0018757 | A1 | 1/2018 | Suzuki |
| 2019/0354850 | A1 | 11/2019 | Watson et al. |
| 2020/0074629 | A1* | 3/2020 | Zur .................. A61B 1/000096 |
| 2020/0297299 | A1 | 9/2020 | Hofmann et al. |
| 2022/0287668 | A1* | 9/2022 | Gulsun .................. G16H 50/20 |
| 2022/0366679 | A1 | 11/2022 | Li et al. |
| 2023/0116897 | A1 | 4/2023 | Hosseinzadeh Taher et al. |

OTHER PUBLICATIONS

Machine translation of WO2014192935A1 (Year: 2014).*

Machine translation of CN-110879949-B obtained from Google Patents (Year: 2023).*

U.S. Appl. No. 17/935,581, "CT Reconstruction for Machine Consumption", filed Sep. 27, 2022, 37 pgs.

Extended European Search Report (EESR) mailed Nov. 11, 2024 in corresponding European Patent Application No. 24186377.8.

* cited by examiner

AI-BASED MEDICAL IMAGING ANALYSIS OF PHOTON COUNTING DATA

TECHNICAL FIELD

The present invention relates generally to medical imaging analysis, and in particular to AI (artificial intelligence)/ML (machine learning)-based medical imaging analysis of photon counting data.

BACKGROUND

Photon counting is a technique in CT (computed tomography) imaging in which spectral imaging data is acquired by counting individual photons using energy-selective photon-counting detectors. Images may be generated from the spectral imaging data with high spatial resolution, without electronic noise, with improved contrast-to-noise ratio, and with spectral information.

Recently, artificial intelligence and machine learning based systems have been proposed for performing various medical imaging analysis tasks on medical images. However, conventional artificial intelligence and machine learning based systems are not suited for processing images generated from spectral imaging data acquired via photon counting.

BRIEF SUMMARY OF THE INVENTION

In accordance with one or more embodiments, systems and methods for performing a medical imaging analysis task from PCCT (photon counting computed tomography) imaging data are provided. PCCT imaging data acquired from a PCCT imaging device is received. A plurality of PCCT virtual images is generated from the PCCT imaging data. A plurality of medical imaging analysis sub-tasks is performed based on the plurality of PCCT virtual images using a plurality of machine learning based networks. Results of the medical imaging analysis sub-tasks are combined to generate results of a medical imaging analysis task. The results of the medical imaging analysis task are output.

In one embodiment, the plurality of PCCT virtual images comprise at least one of virtual monoenergetic images, virtual non-contrast images, virtual iodine images, virtual pure lumen images, and ultra-high-resolution images.

In one embodiment, the results of the medical imaging analysis sub-tasks are combined based on a statistical weighting of the results of the medical imaging analysis sub-tasks. In another embodiment, the results of the medical imaging analysis sub-tasks are combined based on a learned weighting of the results of the medical imaging analysis sub-tasks. The learned weighting is learned based on ground truth data. In another embodiment, the results of the medical imaging analysis sub-tasks are combined based on a context based weighting of the results of the medical imaging analysis sub-tasks.

In one embodiment, the medical imaging analysis task comprises automatic reporting of a coronary artery stenosis and the plurality of medical imaging analysis sub-tasks comprises at least one of detection of coronary artery centerlines, detection of stenoses, grading of stenoses, labelling of vessel segments, and detection of lumen and plaque.

In one embodiment, the medical imaging analysis task comprises at least one of comprise automated CAD-RADS (coronary artery disease reporting and data system) scoring, detection and quantification of coronary plaque and fat, computation of CT-FFR (computed tomography fractional flow reserve), detection of stent and quantification of in-stent restenosis, and detection of bypass graft and assessment of graft patency and the plurality of medical imaging analysis sub-tasks comprises at least one of coronary centerline tracing, lesion detection, segment labeling, lumen and outer wall segmentation, and quantification of plaque components.

These and other advantages of the invention will be apparent to those of ordinary skill in the art by reference to the following detailed description and the accompanying drawings.

DETAILED DESCRIPTION

The present invention generally relates to methods and systems for AI/ML-based medical imaging analysis of photon counting data. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for an AI system for performing a medical imaging analysis task on a plurality of PCCT virtual images. The AI system comprises a plurality of machine learning based networks for performing a plurality of medical imaging analysis sub-tasks based on the plurality of PCCT virtual images. The plurality of PCCT virtual images may be of different types, such a, e.g., monoenergetic images reconstructed from different energy levels, non-contrast images, iodine images, pure lumen images, ultra-high-resolution images, etc. Results of the medical imaging analysis sub-tasks are combined to generate results of the medical imaging analysis task. Advantageously, embodiments described herein process a plurality of PCCT virtual images thereby improving the performance of medical imaging analysis tasks.

Figure 1:
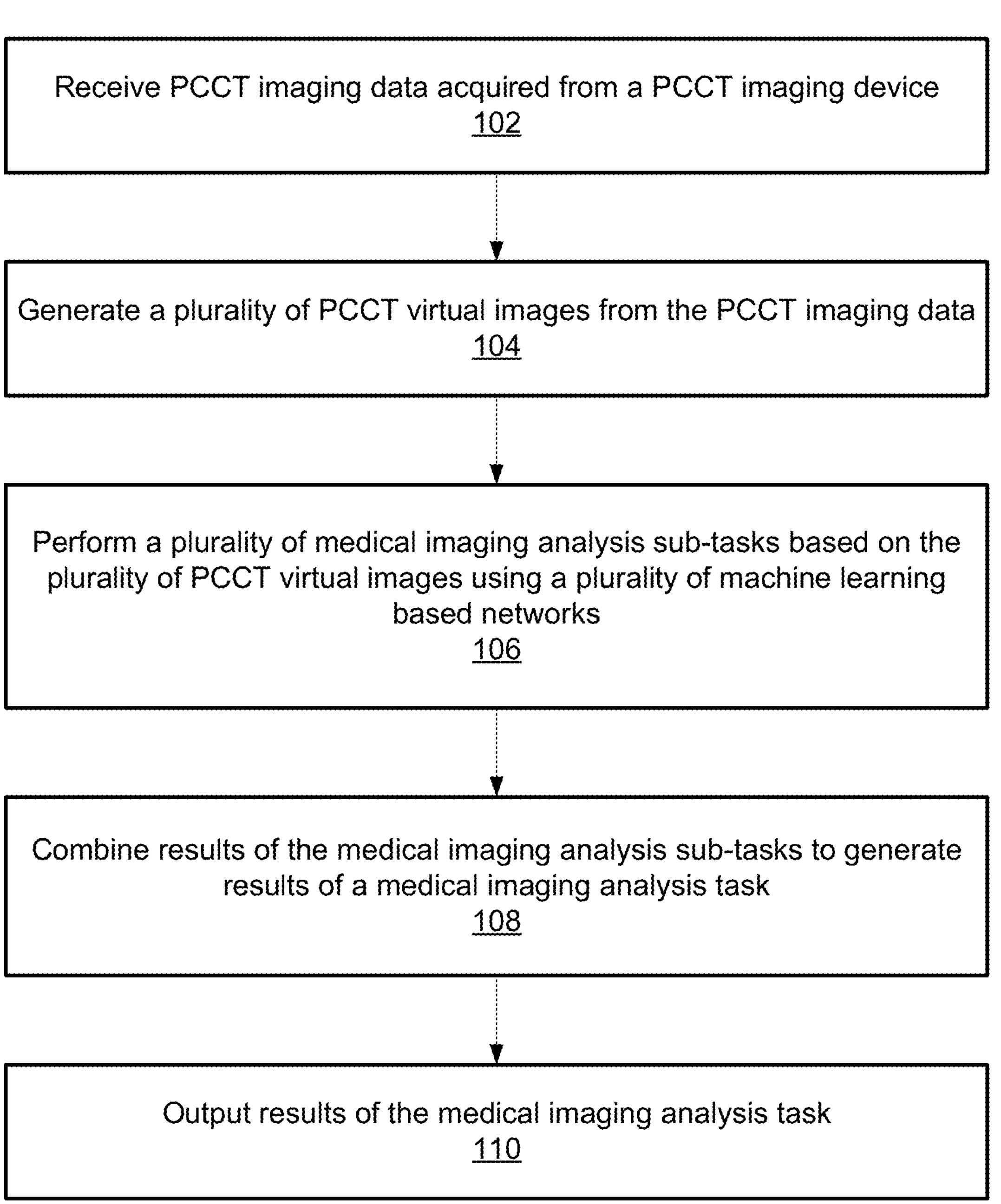
FIG. 1 shows a method for performing a medical imaging analysis task from PCCT imaging data, in accordance with one or more embodiments.
Figure 2:
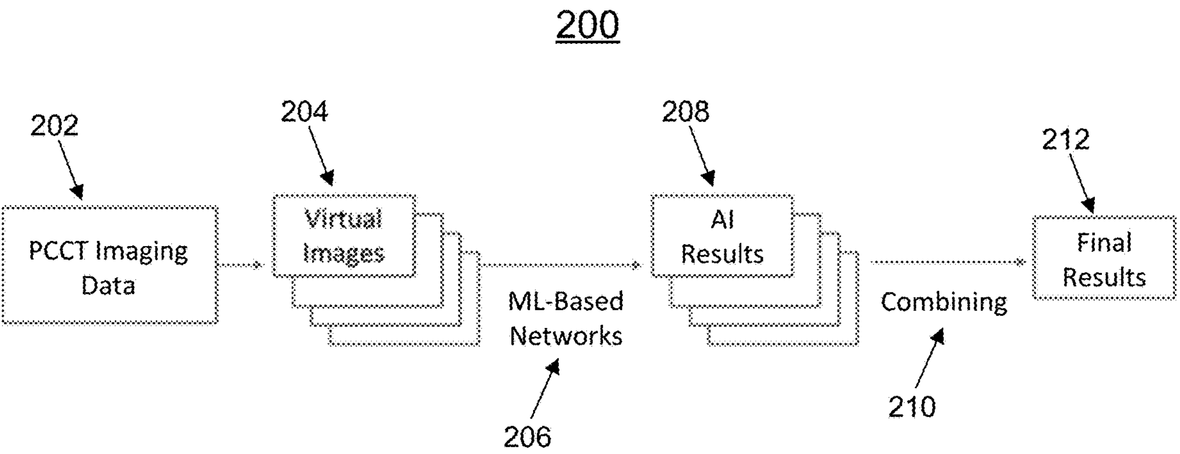
FIG. 2 shows a workflow for performing a medical imaging analysis task from PCCT imaging data, in accordance with one or more embodiments.

FIG. 1 shows a method 100 for performing a medical imaging analysis task from PCCT imaging data, in accordance with one or more embodiments. The steps of method 100 may be performed by one or more suitable computing devices, such as, e.g., computer 602 of FIG. 6. FIG. 2 shows a workflow 200 for performing a medical imaging analysis task from PCCT imaging data, in accordance with one or more embodiments. FIG. 1 and FIG. 2 will be described together.

At step 102 of FIG. 1, PCCT imaging data acquired from a PCCT imaging device is received. The PCCT imaging device is equipped with a photon counting detector for counting the number of incoming photons from an x-ray and directly measuring photon energy. The PCCT imaging data may be imaging data of any anatomical object or objects of interest of a patient, such as, e.g., organs, bones, lesions, etc. In one example, as shown in workflow 200 of FIG. 2, the PCCT imaging data may be PCCT imaging data 202. The PCCT imaging data may be received directly from the PCCT imaging device as the PCCT imaging data is acquired, can be received by loading previously acquired PCCT imaging data from a storage or memory of a computer system, or by receiving the PCCT imaging data from a remote computer system.

At step 104 of FIG. 1, a plurality of PCCT virtual images is generated from the PCCT imaging data. In one example, as shown in workflow 200 of FIG. 2, the plurality of PCCT virtual images is virtual images 204. The plurality of PCCT virtual images may be generated from the PCCT imaging data using any suitable (e.g., known) approach. For example, virtual non-contrast, iodine or pure lumen images can be reconstructed through decomposition of materials such as iodine, calcium, and fat, or virtual monoenergetic images can be reconstructed based on weighting and combining different energy bins available in the spectral data. In addition, small pixel size of photon-counting detectors allows for acquiring ultra-high-resolution images with a slice thickness significantly smaller than the conventional CT.

The plurality of PCCT virtual images may be of different types. For example, the plurality of PCCT virtual images may comprise virtual monoenergetic images reconstructed from different energy levels (e.g., 50 or 100 keV (kiloelectron volt)), virtual non-contrast images, virtual iodine images, virtual pure lumen images that subtract calcium from contrast enhanced scans, ultra-high-resolution images, or any other suitable type of PCCT virtual images.

In one embodiment, the plurality of PCCT virtual images may be enriched based on various acquisition and reconstruction protocol parameters, such as, e.g., reconstruction algorithm and convolution kernels.

At step 106 of FIG. 1, a plurality of medical imaging analysis sub-tasks is performed based on the plurality of PCCT virtual images using a plurality of machine learning based networks. In one embodiment, as shown in workflow 200 of FIG. 2, the plurality of machine learning based networks are ML-based networks 206 that receive as input virtual images 204 and generate as output AI results 208. At least some of the plurality of medical imaging analysis sub-tasks may be performed by different machine learning based networks and/or by the same machine learning based network. The plurality of medical imaging analysis sub-tasks may comprise any suitable imaging analysis task, such as, e.g., segmentation, detection, registration, etc.

Figure 3:
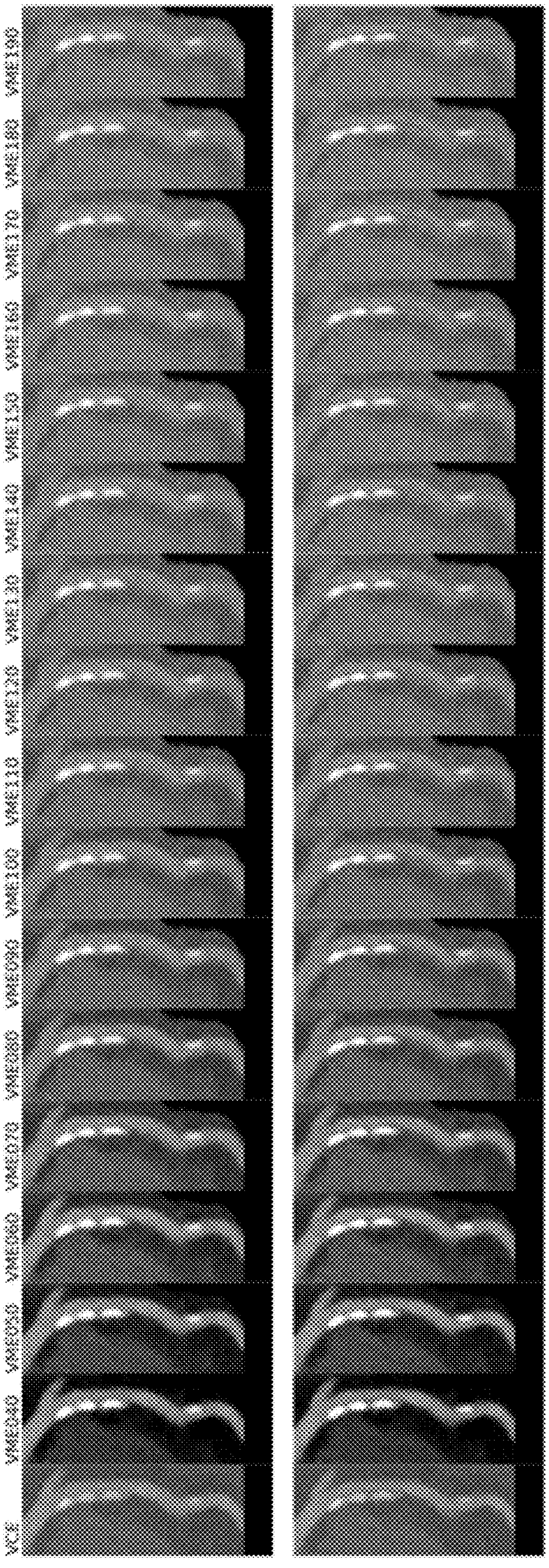
FIG. 3 shows exemplary lumen segmentation results generated from different PCCT virtual images, in accordance with one or more embodiments.

FIG. 3 shows exemplary lumen segmentation results 300 generated from different PCCT virtual images, in accordance with one or more embodiments. Lumen segmentation results 300 are generated by a machine learning based segmentation network performing the medical imaging analysis sub-task of lumen segmentation. The top row shows the PCCT virtual images and the bottom row shows corresponding lumen segmentation results. As can be seen in FIG. 3, the PCCT virtual images comprise a VCE (virtual iodine image) and VME (virtual monoenergetic images) reconstructed from 40 keV to 190 keV energy levels.

Referring back to FIG. 1, the plurality of machine learning based networks may be part of an AI system. The AI system is configured for performing one or more overarching medical imaging analysis tasks by applying each of the plurality of machine learning based networks for performing a respective one of the medical imaging analysis sub-tasks. In one embodiment, the medical imaging analysis task comprises automatic reporting of a coronary artery stenosis and the plurality of medical imaging analysis sub-tasks comprises detection of coronary artery centerlines, detection of stenoses, grading of stenoses, labelling of vessel segments, detection of lumen and plaque, etc. In another embodiment, in the context of coronary applications, the medical imaging analysis tasks comprise at least one of automated CAD-RADS (coronary artery disease reporting and data system) scoring, detection and quantification of coronary plaque and fat, computation of CT-FFR (computed tomography fractional flow reserve), detection of stent and quantification of in-stent restenosis, and detection of bypass graft and assessment of graft patency and the plurality of medical imaging analysis sub-tasks comprises coronary centerline tracing, lesion detection, segment labeling, lumen and outer wall segmentation, and quantification of plaque components.

Each machine learning based network receives as input one or more of the plurality of PCCT virtual images and generates as output results of the medical imaging analysis sub-task. In some embodiments, the machine learning based networks may additionally receive as input one or more outputs generated by one or more other machine learning based networks of the plurality of machine learning based networks. The plurality of machine learning based networks are trained during a prior offline or training stage using any suitable approach. Once trained, the plurality of machine learning based networks are applied during an online or inference stage (e.g., at step 106 of FIG. 1) to perform the plurality of medical imaging analysis sub-tasks.

In one embodiment, instead of the plurality of machine learning based networks, the AI system may comprise non-machine learning based components for performing one or more of the plurality of medical imaging analysis sub-tasks.

At step 108 of FIG. 1, results of the medical imaging analysis sub-tasks are combined to generate results of a medical imaging analysis task. For example, as shown in workflow 200 of FIG. 2, AI results 208 of the medical imaging analysis sub-tasks are combined 210 to generate final results 212 of the medical imaging analysis task. The results of the medical imaging analysis sub-tasks may be combined according to any suitable approach.

In one embodiment, the results of the medical imaging analysis sub-tasks are combined into a single output that yields the best performance on a selected medical imaging analysis task. The combination can be performed either at the AI system level or at the component level for each individual machine learning based network.

In one embodiment, the results of the medical imaging analysis sub-tasks are combined based on a weighting scheme. In one embodiment, the results of the medical imaging analysis sub-tasks are combined based on a statistical weighting, such as, e.g., mean, median, mode, etc. In another embodiment, the results of the medical imaging analysis sub-tasks are combined based on a learned weighting. In this embodiment, weights that optimize a target objective are determined based on expert annotated ground truth data. For the coronary use case, for example, ground truth data may include other modalities such as, e.g., coronary angiogram, OCT (optical coherence tomography), IVUS (intravascular ultrasound), etc. In a further embodiment, the results of the medical imaging analysis sub-tasks are combined via context based weighting. In this embodiment, a particular weighting scheme may be selected based on a disease characteristic or other contextual information. For example, different weighting schemes can be used for segmentation based on plaque composition (calcified or soft). In a further embodiment, the results of the medical imaging analysis sub-tasks are combined via based on a user defined weighting.

At step 110 of FIG. 1, the results of the medical imaging analysis task are output. For example, the results of the medical imaging analysis task can be output by displaying the results of the medical imaging analysis task on a display device of a computer system, storing the results of the medical imaging analysis task on a memory or storage of a computer system, or by transmitting the results of the medical imaging analysis task to a remote computer system.

In one embodiment, one or more of the plurality of PCCT virtual images may be displayed or presented to a user at step 110 of FIG. 1 based on the medical imaging analysis task (e.g., stenosis grading vs. plaque quantification) or disease characteristic (e.g., calcified vs. soft plaque). For example, one or more of the most weighted PCCT virtual images may be selected for displaying to the user.

In one embodiment, a composite image comprising the results of the medical imaging analysis subtasks may be displayed to the user at step 110 of FIG. 1. The composite image may be used for the communication of the results of the medical imaging analysis task of the AI system or for diagnostic assessment.

In one embodiment, at step 106 of FIG. 1, the weighting scheme described with respect to step 108 of FIG. 1 may be directly applied to combine or fuse the plurality of PCCT virtual images. The fused image may be input to the plurality of machine learning based networks for performing the plurality of medical imaging analysis sub-tasks.

In one embodiment, the plurality of machine learning based networks may be run at an operating point that can be estimated at runtime by analyzing the outputs of the machine learning based networks for one or more of the plurality of PCCT virtual images.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is “feature learning”) can be used. In particular, the parameters of the trained machine learning based model can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
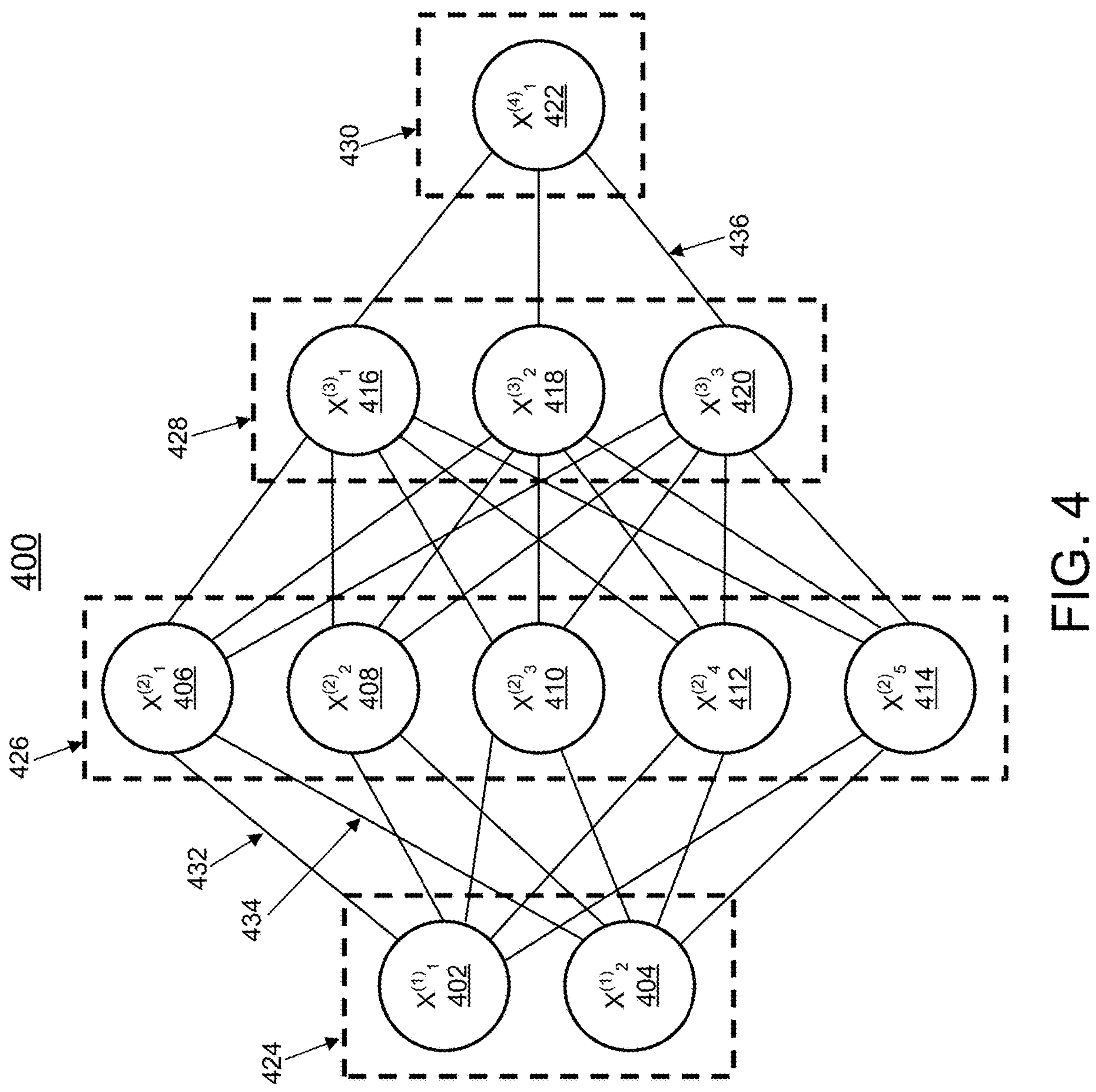
FIG. 4 shows an exemplary artificial neural network that may be used to implement one or more embodiments.

FIG. 4 shows an embodiment of an artificial neural network 400, in accordance with one or more embodiments. Alternative terms for “artificial neural network” are “neural network”, “artificial neural net” or “neural net”. Machine learning networks described herein, such as, e.g., the plurality of machine learning based networks utilized at step 106 of FIG. 1 or the ML-based networks 206 of FIG. 2, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as “ingoing edge” for the second node 402-422 and as “outgoing edge” for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w_{i,j}'^{(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 430, wherein f' is the first derivative of the activation function, and $y^{(n+1)}_j$ is the comparison training value for the j-th node of the output layer 430.

Figure 5:
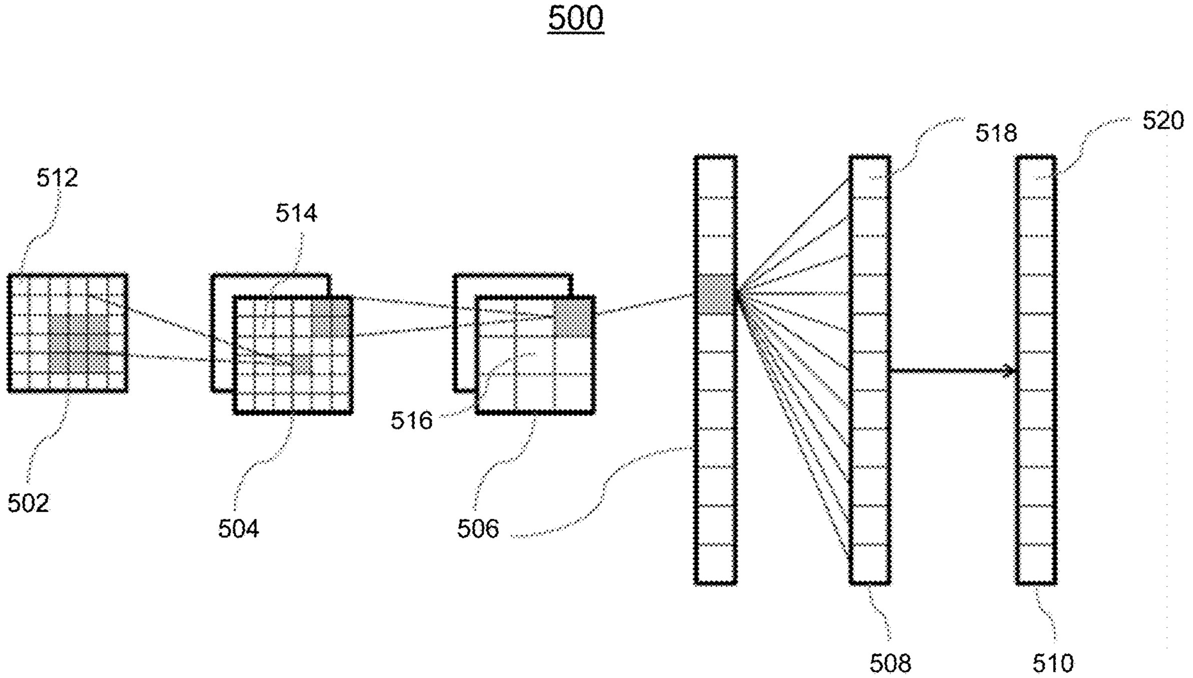
FIG. 5 shows a convolutional neural network that may be used to implement one or more embodiments.

FIG. 5 shows a convolutional neural network 500, in accordance with one or more embodiments. Machine learning networks described herein, such as, e.g., the plurality of machine learning based networks utilized at step 106 of FIG. 1 or the ML-based networks 206 of FIG. 2, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)}[i, j] = \left(K_x * x^{(n-1)}\right)[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j]=f\left(x^{(n-1)}[id_1,jd_2],\ \ldots,\ x^{(n-1)}[id_1+d_1-1,\ jd_2+d_2-1]\right)$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g., dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 2. Certain steps or functions of the methods and workflows described herein, including one or more of the steps or functions of FIG. 1 or 2, may be performed by a server or by another processor in a network-based cloud-computing system. Certain steps or functions of the methods and workflows described herein, including one or more of the steps of FIG. 1 or 2, may be performed by a client computer in a network-based cloud computing system. The steps or functions of the methods and workflows described herein, including one or more of the steps of FIG. 1 or 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
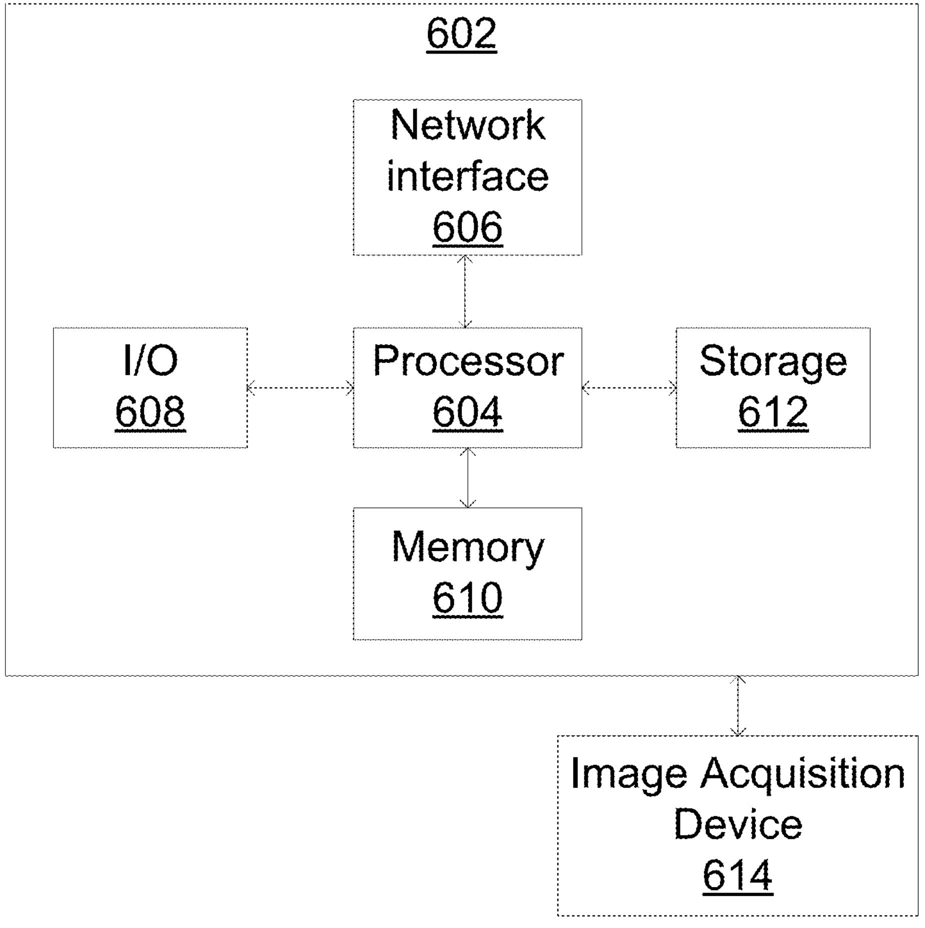
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 or 2 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1 or 2. Accordingly, by executing the computer program instructions, the processor 604 executes the method and workflow steps or functions of FIG. 1 or 2. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:

receiving PCCT (photon counting computed tomography) imaging data acquired from a PCCT imaging device;

generating a plurality of PCCT virtual images based on weighting and combining different energy bins available in the PCCT imaging data;

performing a plurality of medical imaging analysis sub-tasks, wherein each of the plurality of medical imaging analysis sub-tasks is performed based on one or more different PCCT virtual images of the plurality of PCCT virtual images using a different machine learning based network of a plurality of machine learning based networks;

combining results of the medical imaging analysis sub-tasks based on a context based weighting of the results of the medical imaging analysis sub-tasks to generate results of a medical imaging analysis task; and outputting the results of the medical imaging analysis task.

2. The computer-implemented method of claim 1, wherein the plurality of PCCT virtual images comprise at least one of virtual monoenergetic images, virtual non-contrast images, virtual iodine images, virtual pure lumen images, or ultra-high-resolution images.

3. The computer-implemented method of claim 1, wherein the medical imaging analysis task comprises automatic reporting of a coronary artery stenosis and the plurality of medical imaging analysis sub-tasks comprises at least one of detection of coronary artery centerlines, detection of stenoses, grading of stenoses, labelling of vessel segments, or detection of lumen and plaque.

4. The computer-implemented method of claim 1, wherein the medical imaging analysis task comprises at least one of automated CAD-RADS (coronary artery disease reporting and data system) scoring, detection and quantification of coronary plaque and fat, computation of CT-FFR (computed tomography fractional flow reserve), detection of stent and quantification of in-stent restenosis, or detection of bypass graft and assessment of graft patency and the plurality of medical imaging analysis sub-tasks comprises at least one of coronary centerline tracing, lesion detection, segment labeling, lumen and outer wall segmentation, or quantification of plaque components.

5. The computer-implemented method of claim 1, wherein the context based weighting is based on a disease characteristic.

6. An apparatus comprising:

means for receiving PCCT (photon counting computed tomography) imaging data acquired from a PCCT imaging device;

means for generating a plurality of PCCT virtual images based on weighting and combining different energy bins available in the PCCT imaging data;

means for performing a plurality of medical imaging analysis sub-tasks, wherein each of the plurality of medical imaging analysis sub-tasks is performed based on one or more different PCCT virtual images of the plurality of PCCT virtual images using a different machine learning based network of a plurality of machine learning based networks;

means for combining results of the medical imaging analysis sub-tasks based on a context based weighting of the results of the medical imaging analysis sub-tasks to generate results of a medical imaging analysis task; and means for outputting the results of the medical imaging analysis task.

7. The apparatus of claim 6, wherein the plurality of PCCT virtual images comprise at least one of virtual monoenergetic images, virtual non-contrast images, virtual iodine images, virtual pure lumen images, or ultra-high-resolution images.

8. The apparatus of claim 6, wherein the medical imaging analysis task comprises automatic reporting of a coronary artery stenosis and the plurality of medical imaging analysis sub-tasks comprises at least one of detection of coronary artery centerlines, detection of stenoses, grading of stenoses, labelling of vessel segments, or detection of lumen and plaque.

9. The apparatus of claim 6, wherein the medical imaging analysis task comprises at least one of automated CAD-RADS (coronary artery disease reporting and data system) scoring, detection and quantification of coronary plaque and fat, computation of CT-FFR (computed tomography fractional flow reserve), detection of stent and quantification of in-stent restenosis, or detection of bypass graft and assessment of graft patency and the plurality of medical imaging analysis sub-tasks comprises at least one of coronary centerline tracing, lesion detection, segment labeling, lumen and outer wall segmentation, or quantification of plaque components.

10. The apparatus of claim 6, wherein the context based weighting is based on a disease characteristic.

11. A non-transitory computer readable medium storing computer program instructions, the computer program instructions when executed by a processor cause the processor to perform operations comprising:

receiving PCCT (photon counting computed tomography) imaging data acquired from a PCCT imaging device;

generating a plurality of PCCT virtual images based on weighting and combining different energy bins available in the PCCT imaging data;

performing a plurality of medical imaging analysis sub-tasks, wherein each of the plurality of medical imaging analysis sub-tasks is performed based on one or more different PCCT virtual images of the plurality of PCCT virtual images using a different machine learning based network of a plurality of machine learning based networks;

combining results of the medical imaging analysis sub-tasks based on a context based weighting of the results of the medical imaging analysis sub-tasks to generate results of a medical imaging analysis task; and outputting the results of the medical imaging analysis task.

12. The non-transitory computer readable medium of claim 11, wherein the plurality of PCCT virtual images comprise at least one of virtual monoenergetic images, virtual non-contrast images, virtual iodine images, virtual pure lumen images, or ultra-high-resolution images.

13. The non-transitory computer readable medium of claim 11, wherein the medical imaging analysis task comprises automatic reporting of a coronary artery stenosis and the plurality of medical imaging analysis sub-tasks comprises at least one of detection of coronary artery centerlines, detection of stenoses, grading of stenoses, labelling of vessel segments, or detection of lumen and plaque.

14. The non-transitory computer readable medium of claim 11, wherein the context based weighting is based on a disease characteristic.

* * * * *